(12) United States Patent
Loussides et al.

(10) Patent No.: US 9,786,189 B2
(45) Date of Patent: Oct. 10, 2017

(54) AIRCRAFT CONTROL SYSTEMS

(71) Applicant: Sikorsky Aircraft Corp., Stratford, CT (US)

(72) Inventors: George N. Loussides, Branford, CT (US); Matthew Zywiak, Durham, CT (US)

(73) Assignee: Sikorsky Aircraft Corp., Lakewood Ranch, FL (US)

( * ) Notice: Subject to any disclaimer, the term of this patent is extended or adjusted under 35 U.S.C. 154(b) by 0 days.

(21) Appl. No.: 15/005,532

(22) Filed: Jan. 25, 2016

(65) Prior Publication Data
US 2017/0213467 A1    Jul. 27, 2017

(51) Int. Cl.
| | | |
|---|---|---|
| G06G 7/70 | (2006.01) | |
| G05D 1/00 | (2006.01) | |
| G08G 5/02 | (2006.01) | |
| G08G 5/00 | (2006.01) | |
| G05D 1/10 | (2006.01) | |
| A61B 5/00 | (2006.01) | |
| A61B 5/18 | (2006.01) | |
| A61B 5/024 | (2006.01) | |
| A61B 5/021 | (2006.01) | |
| A61B 5/11 | (2006.01) | |

(52) U.S. Cl.
CPC ............. *G08G 5/02* (2013.01); *A61B 5/0059* (2013.01); *A61B 5/18* (2013.01); *A61B 5/7282* (2013.01); *G05D 1/0088* (2013.01); *G05D 1/101* (2013.01); *G08G 5/0039* (2013.01); *A61B 5/021* (2013.01); *A61B 5/024* (2013.01); *A61B 5/11* (2013.01); *A61B 5/441* (2013.01)

(58) Field of Classification Search
USPC ...................................................... 701/16, 3
See application file for complete search history.

(56) References Cited

U.S. PATENT DOCUMENTS

| | | | |
|---|---|---|---|
| 7,792,615 B2 | 9/2010 | Aimar | |
| 8,108,086 B2 * | 1/2012 | Bailly | ................ B64D 45/0015 701/14 |
| 8,164,464 B2 | 4/2012 | Matos | |
| 8,761,965 B2 | 6/2014 | Righi et al. | |
| 8,892,274 B2 | 11/2014 | Baudry | |
| 9,043,043 B1 * | 5/2015 | Gribble | ................ G05D 1/0061 701/1 |

(Continued)

FOREIGN PATENT DOCUMENTS

EP    1422680 A2    5/2004

OTHER PUBLICATIONS

Extended European Search Report, issued by Examiner Philippe Mallet, of the European Patent Office, dated May 17, 2017, in corresponding European Patent Application No. 16200178.8.

*Primary Examiner* — Tyler Paige
(74) *Attorney, Agent, or Firm* — Locke Lord LLP; Daniel J. Fiorello; Joshua L. Jones

(57) ABSTRACT

A method of controlling an aircraft in the event of pilot incapacity includes detecting, using at least one sensor, the occurrence of an event relating to a pilot's capacity to control the aircraft, determining whether the event justifies a controlled takeover of the aircraft from the pilot, asserting a controlled takeover of the aircraft from the pilot if it has been determined that a controlled takeover is justified, and executing a controlled landing of the aircraft without assistance of the pilot.

17 Claims, 2 Drawing Sheets

(56) References Cited

U.S. PATENT DOCUMENTS

| | | | |
|---|---|---|---|
| 2003/0093187 A1* | 5/2003 | Walker | B64C 13/20 701/1 |
| 2003/0093193 A1* | 5/2003 | Pippenger | B64D 45/0015 701/3 |
| 2003/0128122 A1 | 7/2003 | Reynolds | |
| 2003/0130770 A1 | 7/2003 | Matos | |
| 2004/0260470 A1* | 12/2004 | Rast | G06Q 10/06 701/300 |
| 2005/0202375 A1 | 9/2005 | Nevo et al. | |
| 2009/0179114 A1* | 7/2009 | Conner | B64D 45/0015 244/189 |
| 2009/0319104 A1* | 12/2009 | Bailly | B64D 45/0015 701/16 |
| 2011/0224849 A1* | 9/2011 | Braly | G05D 1/0061 701/9 |
| 2012/0116610 A1 | 5/2012 | Righi et al. | |
| 2012/0215384 A1* | 8/2012 | Fritz | G05D 1/0061 701/2 |
| 2013/0138270 A1* | 5/2013 | Christensen | G05D 1/102 701/3 |

* cited by examiner

AIRCRAFT CONTROL SYSTEMS

BACKGROUND

1. Field

The present disclosure relates to aircraft, more specifically to aircraft control systems.

2. Description of Related Art

Autopilot systems for aircraft exist in a great majority of civilian and military airplanes and make it possible, for example, to follow a pre-established flight plan, fly at a given altitude, follow a heading chosen by the pilot. These systems reduce the cockpit workload of the pilot. However, the pilot must always be the initiator of an airplane guidance task (e.g., entering the flight plan into the airplane navigation system, choosing the altitude, speed, and other set points) that the automatic piloting systems must then follow. An interaction between the pilot and the automatic piloting systems is therefore necessary to fly an aircraft until it has landed and come to a complete stop.

In certain situations, the pilot may become incapacitated (e.g., due to a failure of a critical system like the airplane pressurization system) and the pilot can no longer pilot the aircraft, particularly in the case of loss of consciousness. In such a situation, the aircraft is left to itself, and if the pilot fails to regain consciousness in time or if control is not regained by another suitable person, the aircraft will ultimately crash.

Furthermore, if the pilot loses consciousness when the automatic pilot is engaged, the flight continues until all the fuel on board is consumed before the airplane crashes. This is because, even when the automatic pilot is engaged, actions on the part of the pilots are necessary to engage an automatic landing phase.

Such conventional methods and systems have generally been considered satisfactory for their intended purpose. However, there is still a need in the art for improved aircraft control systems. The present disclosure provides a solution for this need.

SUMMARY

A method of controlling an aircraft in the event of pilot incapacity includes detecting, using at least one sensor, the occurrence of an event relating to a pilot's capacity to control the aircraft, determining whether the event justifies a controlled takeover of the aircraft from the pilot, asserting a controlled takeover of the aircraft from the pilot if it has been determined that a controlled takeover is justified, and executing a controlled landing of the aircraft without assistance of the pilot.

Detecting the occurrence of an event can include detecting a biometric parameter using the sensor. In certain embodiments, determining whether the event justifies a controlled takeover can include determining whether the biometric parameter is outside of a predetermined range.

In certain embodiments, detecting the occurrence of an event can include detecting aircraft course and/or location information. Determining whether the event justifies a controlled takeover can include determining whether the course information represents a deviation from a predetermined flight course beyond a deviation threshold.

In certain embodiments, detecting the occurrence of an event can include detecting an aircraft flight state. Determining whether the event justifies a controlled takeover can include determining whether the aircraft flight state is within predetermined aircraft operational parameters. Detecting the occurrence of an event can include detecting an action initiated by the pilot or other crew member.

Determining whether the event justifies a controlled takeover can include providing a signal to the pilot indicating that an event has occurred justifying a controlled takeover to confirm whether the pilot is incapacitated. Determining whether the event justifies a controlled takeover can include confirming whether the pilot is incapacitated by remote visual observation.

In certain embodiments, determining whether the event necessitates a controlled takeover can include confirming whether the pilot is incapacitated by illuminating the pilot with a laser and analyzing the reflected light. Asserting a controlled takeover of the aircraft from the pilot can include activating an autonomous flight control of the aircraft. In certain embodiments, asserting a controlled takeover of the aircraft from the pilot involves asserting remote flight control of the aircraft.

Executing a controlled landing of the aircraft without the assistance of the pilot can include flying the aircraft to a predetermined landing location. In certain embodiments, executing a controlled landing of the aircraft without the assistance of the pilot can include flying the aircraft to the closest safe landing area.

In accordance with at least one aspect of this disclosure, an aircraft emergency control system includes a controller operatively connected to at least one sensor to receive a signal therefrom and a flight control system of the aircraft to control the aircraft. The controller can include a processor, a memory, and instructions executable by the processor to perform the entirety or any suitable portion of a method as described herein.

These and other features of the systems and methods of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
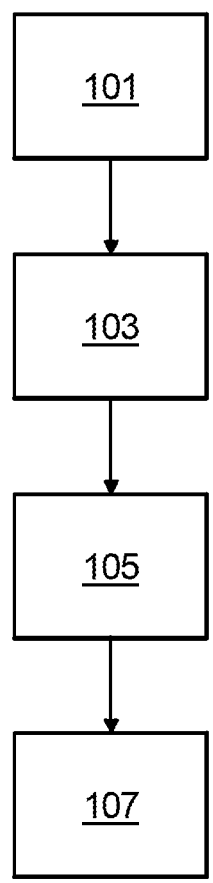
FIG. 1 is a block diagram of an embodiment of a method in accordance with this disclosure.
Figure 2:
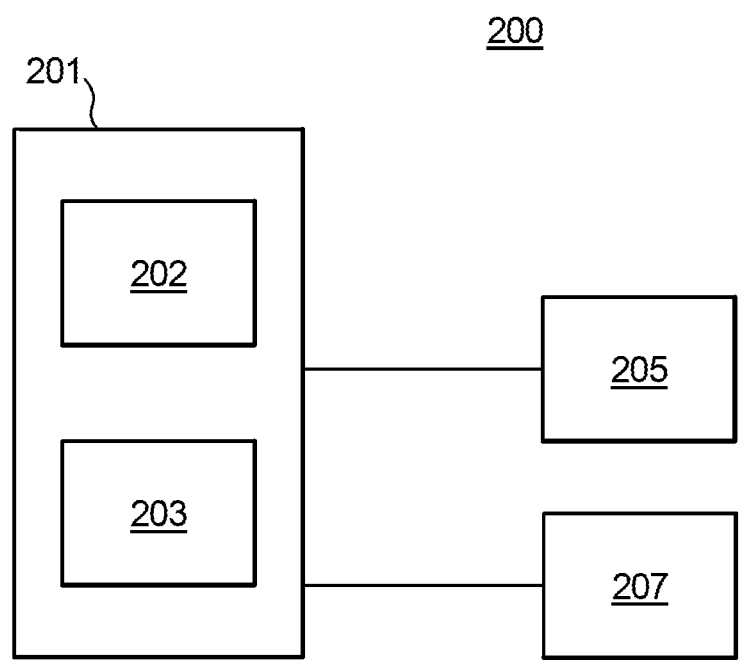
FIG. 2 is schematic diagram of an embodiment of a controller in accordance with this disclosure, shown operatively connected to a flight system of an aircraft.

Reference will now be made to the drawings wherein like reference numerals identify similar structural features or aspects of the subject disclosure. For purposes of explanation and illustration, and not limitation, an illustrative view of an embodiment of a method in accordance with the disclosure is shown in FIG. 1 and is designated generally by reference character 100. Other embodiments and/or aspects of this disclosure are shown in FIG. 2. The systems and methods described herein can be used to control an aircraft (e.g., in the event of pilot incapacity).

Referring to FIG. 1, a method 100 of controlling an aircraft in the event of pilot incapacity includes detecting (e.g., at block 101) the occurrence of an event relating to a pilot's capacity to control the aircraft. Detecting (e.g., at block 101) the occurrence of an event can include using at least one sensor (e.g., a sensor 205, as shown in FIG. 2, disposed in the cockpit of the aircraft).

Detecting (e.g., at block 101) the occurrence of an event can include detecting a biometric parameter (e.g., heart rate, blood pressure, consciousness, skin color, head position, body position) using the sensor 205. In certain embodiments, detecting (e.g., at block 101) the occurrence of an event can include detecting aircraft course and/or location information (e.g., using a GPS).

In certain embodiments, detecting (e.g., at block 101) the occurrence of an event can include detecting an aircraft flight state (e.g., pitch, roll, yaw, airspeed, angle of attack, control inputs, throttle, engine condition, oxygen level in the cockpit/other parts of the aircraft). Detecting (e.g., at block 101) the occurrence of an event can include detecting an action initiated by the pilot or other crew member (e.g., an abrupt maneuver outside of usual or expected inputs).

The method 100 further includes determining (e.g., at block 103) whether the event justifies a controlled takeover of the aircraft from the pilot. Determining (e.g., at block 103) whether the event justifies a controlled takeover can include determining whether course information and/or location of the aircraft represents a deviation from a predetermined flight course beyond a deviation threshold (e.g., a predetermined amount of nautical miles or time at cruise).

In certain embodiments, determining (e.g., at block 103) whether the event justifies a controlled takeover can include determining whether a biometric parameter of the pilot is outside of a predetermined range (e.g., the pilot's heartbeat becomes to slow or stops, the pilot's skin/lips turns bluish, the pilot's eyes close too frequently and/or for too long of a period of time, the pilot's head and/or body slumps for a predetermined period of time, the pilot's eye movement is indicative of dissociation/hypoxia, the pilot's breathing is abnormal, or any other suitable biometric indicator that the pilot is incapacitated). For example, a profile of normal biometric parameters for a pilot can be created and/or stored and compared against readings from the sensor 205 to evaluate whether the sensed biometric parameters deviate from the profile.

In certain embodiments, determining (e.g., at block 103) whether the event justifies a controlled takeover can include determining whether the aircraft flight state is within predetermined aircraft operational parameters. For example, it can be determined whether the aircraft is turning, climbing, and/or descending too abruptly, severely, and/or in an unexpected or unsafe manner.

Determining (e.g., at block 103) whether the event justifies a controlled takeover can include confirming whether the pilot is incapacitated by remote visual observation. For example, the sensor 205 can include a video camera configured to provide at least a partial view of the cockpit and/or a pilot which can be remotely accessed by another crew member or by support crew on the ground (e.g., air traffic control). This can also allow intervention in the event of hijacking, for example.

Determining (e.g., at block 103) whether the event justifies a controlled takeover can include providing a signal to the pilot indicating that an event has occurred justifying a controlled takeover to confirm whether the pilot is incapacitated. For example, if the pilot is detected as potentially being hypoxic or asleep, an audible indicator and/or visual indicator can activate to try to catch the pilot's attention. The indicator can be temporarily deactivated by physical interaction by the pilot (e.g., if the pilot determines the indicator is in error). If the pilot does not react, it can be determined that the pilot is incapacitated.

In certain embodiments, determining whether the event necessitates a controlled takeover can include confirming whether the pilot is incapacitated by illuminating the pilot with a laser and analyzing the reflected light (e.g., for any suitable biometric parameter detectable by such methods). It is also contemplated that the pilot can indicate (e.g., by activating a switch or button) that imminent incapacitation is likely.

The method 100 further includes asserting (e.g., at block 105) a controlled takeover of the aircraft from the pilot if it has been determined that a controlled takeover is justified. In certain embodiments, asserting a controlled takeover of the aircraft from the pilot can include activating an autonomous flight control (e.g., in flight control system 207) of the aircraft. In certain embodiments, asserting (e.g., at block 105) a controlled takeover of the aircraft from the pilot involves asserting remote flight control of the aircraft such that a remote crew member or support crew on the ground (e.g., air traffic control) can fly the aircraft remotely.

The method 100 further includes executing (e.g., at block 107) a controlled landing of the aircraft without assistance of the pilot. Executing (e.g. at block 107) a controlled landing of the aircraft without the assistance of the pilot can include flying the aircraft to a predetermined landing location. In certain embodiments, executing (e.g., at block 107) a controlled landing of the aircraft without the assistance of the pilot can include flying the aircraft to the closest safe landing area (e.g., by flying directly to the nearest airport having a sufficiently long runway for the aircraft to safely land, by locating a safe landing site near by using on board perception).

Any other suitable maneuvers as part of flying the aircraft to a safe landing zone or other safe zone (e.g., below about 12,500 feet of density altitude in the event of decompression or low oxygen level in the cockpit to allow a hypoxic pilot to regain consciousness or control of the aircraft) are contemplated herein. For example, a suitable landing zone may not be available for one or more reasons (lack of fuel, engine failure), at which point a best option crash site can be determined, considering one or more flight factors (e.g., wind direction, altitude remaining vs. glide ratio) and/or one or more crash site factors (e.g., to select water instead of trees, flatland instead of mountainous terrain, and/or unpopulated areas instead of populated areas).

In accordance with at least one aspect of this disclosure, referring to FIG. 2, an aircraft emergency control system 200 includes a controller 201 operatively connected to at least one sensor 205 to receive a signal therefrom. The sensor 205 can include any suitable sensor for sensing a condition of the pilot and/or the aircraft (e.g., a laser emitter and receiver such as a LIDAR system, a video camera). In certain embodiments, the sensor 205 can include any suitable biometric sensor (e.g., a heartbeat sensor, a skin color sensor, an eye position/movement sensor, an eye lid sensor, a breathing rate sensor, a sweating sensor). The sensor 205 can include a responsiveness sensor to detect a time since a pilot last operated a control (e.g., yoke, pedals, throttle) or since last voice communication. In certain embodiments, the sensor 205 can include an aircraft state sensor (e.g., a GPS configured to detect a position/speed of an aircraft, a roll, pitch, and/or yaw sensor).

The controller 201 is also operatively connected to a flight control system 207 of an aircraft to control the aircraft. In certain embodiments, at least a portion of sensor 205 can be a part of the flight control system 207 (e.g., because certain avionics include certain aircraft state sensors already) or can be entirely separate from the flight control system 207.

The controller 201 can include a processor 202, a memory 203. The memory 203 includes instructions stored thereon that are executable by the processor 202 to perform the entirety of or any suitable portion of a method 100 as described above. The controller 201 can include any other suitable hardware and/or software as understood by those having ordinary skill in the art.

As described above, a determination of when a pilot can no longer control the aircraft can be made and control of the aircraft can be reassigned to a predetermined control scheme or to a remote party. Such embodiments can allow for a plane to be safely controlled and/or landed even in the event of pilot incapacity due to any reason. This can avoid loss of life by avoiding a catastrophic crash. Additionally aircraft and or property damage would be avoided.

The methods and systems of the present disclosure, as described above and shown in the drawings, provide for aircraft control systems with superior properties including emergency aircraft control. While the apparatus and methods of the subject disclosure have been shown and described with reference to embodiments, those skilled in the art will readily appreciate that changes and/or modifications may be made thereto without departing from the spirit and scope of the subject disclosure.

What is claimed is:

1. A method of controlling an aircraft in the event of pilot incapacity, comprising:
    detecting, using at least one sensor, the occurrence of an event relating to a pilot's capacity to control the aircraft;
    determining, using a controller that is operatively connected to the at least one sensor, whether the event justifies a controlled takeover of the aircraft from the pilot;
    asserting a controlled takeover of the aircraft from the pilot if it has been determined that a controlled takeover is justified; and
    executing a controlled landing of the aircraft without assistance of the pilot.

2. The method of claim 1, wherein detecting the occurrence of an event includes detecting a biometric parameter using the sensor.

3. The method of claim 2, wherein determining whether the event justifies a controlled takeover includes determining whether the biometric parameter is outside of a predetermined range.

4. The method of claim 1, wherein detecting the occurrence of an event includes detecting aircraft course and/or location information.

5. The method of claim 4, wherein determining whether the event justifies a controlled takeover includes determining whether the course information represents a deviation from a predetermined flight course beyond a deviation threshold.

6. The method of claim 1, wherein detecting the occurrence of an event includes detecting an aircraft flight state.

7. The method of claim 6, wherein determining whether the event justifies a controlled takeover includes determining whether the aircraft flight state is within predetermined aircraft operational parameters.

8. The method of claim 1, wherein detecting the occurrence of an event includes detecting an action initiated by the pilot or other crew member.

9. The method of claim 1, wherein determining whether the event justifies a controlled takeover includes providing a signal to the pilot indicating that an event has occurred justifying a controlled takeover to confirm whether the pilot is incapacitated.

10. The method of claim 1, wherein determining whether the event justifies a controlled takeover includes confirming whether the pilot is incapacitated by remote visual observation.

11. The method of any of claim 1, wherein determining whether the event necessitates a controlled takeover includes confirming whether the pilot is incapacitated by illuminating the pilot with a laser and analyzing the reflected light.

12. The method of any of claim 1, wherein asserting a controlled takeover of the aircraft from the pilot includes activating an autonomous flight control of the aircraft.

13. The method of any of claim 1, wherein asserting a controlled takeover of the aircraft from the pilot involves asserting remote flight control of the aircraft.

14. The method of any of claim 1, wherein executing a controlled landing of the aircraft without the assistance of the pilot includes flying the aircraft to a predetermined landing location.

15. The method of any of claim 1, wherein the executing a controlled landing of the aircraft without the assistance of the pilot includes flying the aircraft to the closest safe landing area.

16. An aircraft emergency control system, comprising:
    a controller operatively connected to at least one sensor to receive a signal therefrom and a flight control system of the aircraft to control the aircraft, wherein the controller includes a processor, a memory, and instructions executable by the processor to perform a method, the method including:
        detecting, using the at least one sensor, the occurrence of an event relating to a pilot's capacity to control the aircraft;
        determining whether the event justifies a controlled takeover of the aircraft from the pilot, wherein determining whether the event justifies a controlled takeover includes at least one of determining whether a biometric parameter of the pilot is outside of a predetermined range, determining whether course information and/or location of the aircraft represents a deviation from a predetermined flight course beyond a deviation threshold, determining whether the aircraft flight state is within predetermined aircraft operational parameters, receiving a signal confirming whether the pilot is incapacitated by remote visual observation, providing a signal to the pilot indicating that an event has occurred to confirm whether the pilot is incapacitated and determining whether the pilot reacts, illuminating the pilot with a laser and analyzing the reflected light, or receiving an indication from the pilot that imminent incapacitation is likely;
        asserting a controlled takeover of the aircraft from the pilot if it has been determined that a controlled takeover is justified; and
        executing a controlled landing of the aircraft without assistance of the pilot.

17. The system of claim 16, wherein the at least one sensor includes at least one of a biometric sensor, an aircraft state sensor, an imaging device, a responsiveness sensor, or an aircraft location sensor.

* * * * *